(12) United States Patent
Trinquet et al.

(10) Patent No.: US 7,872,243 B2
(45) Date of Patent: Jan. 18, 2011

(54) METHOD FOR IMPROVING THE DETECTION OF FLUORESCENCE SIGNALS DURING A RESONANCE ENERGY TRANSFER

(75) Inventors: Eric Trinquet, Pont St Esprit (FR); Gérard Mathis, Bagnols sur Ceze (FR)

(73) Assignee: CIS BIO International, Saclay (FR)

( * ) Notice: Subject to any disclaimer, the term of this patent is extended or adjusted under 35 U.S.C. 154(b) by 386 days.

(21) Appl. No.: 11/571,331

(22) PCT Filed: Jun. 27, 2005

(86) PCT No.: PCT/FR2005/001618

§ 371 (c)(1),
(2), (4) Date: Apr. 10, 2009

(87) PCT Pub. No.: WO2006/010839

PCT Pub. Date: Feb. 2, 2006

(65) Prior Publication Data

US 2009/0294691 A1    Dec. 3, 2009

(30) Foreign Application Priority Data

Jun. 28, 2004 (FR) .................................. 04 07087

(51) Int. Cl.
*G01J 1/58* (2006.01)

(52) U.S. Cl. ................................. 250/458.1; 250/459.1

(58) Field of Classification Search ............. 250/458.1, 250/459.1
See application file for complete search history.

(56) References Cited

U.S. PATENT DOCUMENTS

2003/0058442 A1    3/2003    Garab et al.

FOREIGN PATENT DOCUMENTS

| WO | WO 2006/010839 A2 | 2/2006 |
|----|-------------------|--------|
| WO | WO 2006/010839 A3 | 2/2006 |

OTHER PUBLICATIONS

"Quantitative Fluorescence Resonance Energy Transfer Measurements Using Fluorescence Microscopy," Gerald W. Gordon et al., *Biophysical Journal*—May 1998, vol. 74, pp. 2702-2713 (XP-000990953).

(Continued)

*Primary Examiner*—David P Porta
*Assistant Examiner*—Mark R Gaworecki
(74) *Attorney, Agent, or Firm*—Hunton & Williams LLP

(57) ABSTRACT

The invention concerns the use of the fluorescence polarization phenomenon to improve detection of fluorescent signals during a fluorescence resonance energy transfer (FRET). In particular, the invention concerns a method for improving signal/noise ratio in a FRET measurement. The invention also concerns an apparatus for measuring fluorescence following an energy transfer between a donor fluorescent compound and an acceptor fluorescence compound in a measurement medium.

24 Claims, 1 Drawing Sheet

A: standard fluorescence (without polarizers)
B: orthogonal polarized fluorescence

OTHER PUBLICATIONS

"Homo-FRET Microscopy in Living Cells to Measure Monomer-Dimer Transition of GFP-Tagged Proteins," I. Gautier et al., *Biophysical Journal*—Jun. 2001, vol. 80, pp. 3000-3008 (XP-002977865).

"Reliable and Global Measurement of Fluorescence Resonance Energy Transfer Using Fluorescence Microscopes," Zongping Xia et al., Biophysical Journal—Oct. 2001, vol. 81, pp. 2395-2402 (XP-002328970).

"Fluorescence Resonance Energy Transfers Measurements on Cell Surfaces via Fluorescence Polarization," Meir Cohen-Kashi et al., *Biophysical Journal*—Sep. 2002, vol. 83, pp. 1395-1402 (XP-002328968).

"Detection of Tryptophan to Tryptophan Energy Transfer in Proteins," Pierre Moens et al., *The Protein Journal*, Jan. 2004, vol. 23, No. 1, pp. 79-83 (XP-002328973).

English Abstract of JP 2002/098638 published Apr. 5, 2002.

METHOD FOR IMPROVING THE DETECTION OF FLUORESCENCE SIGNALS DURING A RESONANCE ENERGY TRANSFER

The invention relates to the use of the fluorescence polarization phenomenon, in order to improve detection of fluorescence signals during a resonance energy transfer (FRET). In particular, the invention relates to a method for improving the signal/noise ratio in a FRET measurement.

BACKGROUND OF INVENTION

Fluorescence resonance energy transfer (FRET) is a spectroscopic tool widely used in the detection of biological events and in particular of molecular interactions.

In numerous cases, the FRET, which requires bringing close together the donor and acceptor fluorescent molecules which will be involved in the energy transfer, proves to be a powerful tool in the detection of biological interactions. It can be used in fields as varied as molecular biology, the in-vitro or in-cellulo detection of enzymatic phenomena (peptide cleavage, phosphorylation) or interactions between proteins (1, 2, 3).

Detection of the FRET phenomenon can be carried out by measuring different parameters of the fluorescence signal emitted either by the donor, or by the acceptor, or by both molecules. Among the most common techniques, there can in particular be mentioned:

- measurement of the reduction in the donor's fluorescence induced by the FRET phenomenon (4),
- measurement of the increase in the acceptor's fluorescence induced by the energy originating from the donor via the FRET (5),
- determination of the [(acceptor fluorescence increase)/(donor fluorescence reduction)] ratio (6),
- measurement of the reduction in the lifetime of the donor's fluorescence induced by the FRET phenomenon (7). The latter is in particular measured by the "Fluorescence Lifetime Imaging Microscopy" (FLIM) technique,
- measurement of the increase in the fluorescence of the donor involved in a FRET after the photobleaching of the acceptor (8); this photobleaching technique is known as Fluorescence Recovery After Photobleaching (FRAP).

Leaving aside techniques combining the FRET and time-resolved detection made possible by the use of fluorescence donors with a long lifetime (e.g.: HTRF), the FRET phenomenon proves complex to detect in numerous applications based on fluorescence intensity measurements. The need for significant energy compatibility between the donor and the acceptor often leads to the use of molecules possessing relatively similar fluorescence emission spectra. The resulting overlap of the donor's and acceptor's spectra make it very difficult to precisely measure variations in signals recorded on the donor or on the acceptor (9).

This is particularly true when fluorescent proteins derived from Green Fluorescent Protein (GFP) are used in the FRET experiments, such as the Cyan Fluorescent Protein (CFP)/Yellow Fluorescent Protein (YFP) donor/acceptor pair which is the most used. These molecules, which are capable of being expressed in fluorescent form in numerous types of cell, allow the detection of numerous intracellular events. However, a significant overlap of fluorescence spectra exists between the latter, resulting in the direct parasitic excitation of the acceptor by the donor molecule's excitation beam. Therefore, the signal/noise ratio of the FRET experiments carried out with this donor/acceptor pair is low, often less than 1.5 (1). As a result, it is necessary to implement complex experimentation protocols comprising numerous experimental controls in order to be able to interpret the results obtained.

The technical problem to be resolved therefore involves providing a simple and reproducible method for correcting the FRET measurement, in particular by improving the signal/noise ratio.

It has now been found that the impact of the strong overlap of the donor's and acceptor's fluorescence emission spectra could be significantly reduced using the polarization properties of these compounds in order to correct the FRET measurement.

It has been described that the appearance of an energy transfer between two fluorescent molecules caused polarization modifications both at the level of the donor and at the level of the acceptor: the polarization of the donor increases when it is involved in a FRET (10), whereas that of the acceptor involved in the FRET decreases (11).

The influence of the FRET on the relative polarization of the donor and the acceptor has thus been used in different molecular systems in order to detect this energy transfer between two fluorescent probes.

In particular, a homoFRET between two GFP molecules has been detected by measuring their depolarization (12). Measurement of the depolarization of rhodamine coupled to a lectin was used to detect a FRET being produced between the fluorescein and the rhodamine (5). Also, measurement of the increase in the polarization of a Concanavilin A-Fluorescein donor made it possible to detect a FRET indicating the formation of a molecular cluster in the lymphocyte membranes (10).

The polarization measurements used thus far therefore had the purpose of detecting the existence of a FRET between two molecules.

BRIEF SUMMARY OF THE INVENTION

Figure 1:
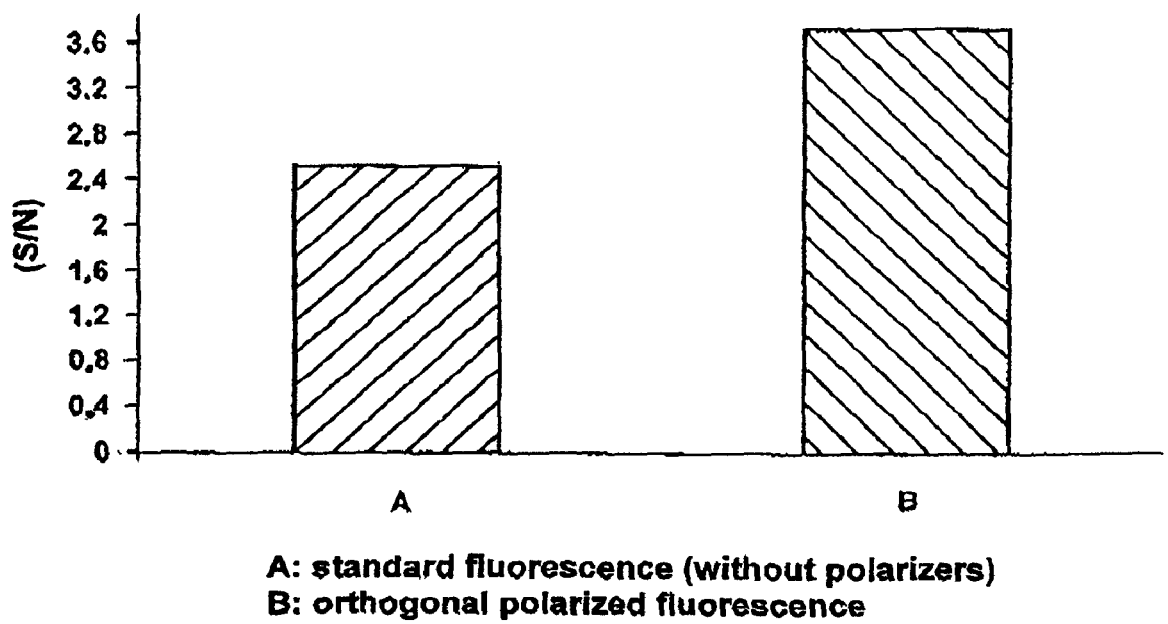
FIG. 1 depicts a graph of signal/noise values obtained in both the absence and the presence of polarizers.

Surprisingly, it has now been found that the polarized measurement of the fluorescence signals makes it possible to better isolate the signals emitted specifically by the donor and the acceptor involved in the FRET and therefore to increase the signal/noise ratio in the tests carried out.

In fact, the fluorescent proteins of GFP type for example, due to their structure and their molecular weight, are strongly polarized molecules. Their degree of polarization varies when they are involved in an energy transfer: as donor molecule, their polarization increases a little, whereas, as acceptor molecule, they undergo a strong depolarization through the FRET phenomenon.

In a medium containing a donor fluorescent compound and an acceptor fluorescent compound and where an energy transfer takes place between these two compounds following the excitation of the medium at the donor's excitation wavelength, the signal measured at the acceptor's emission wavelength comprises:

- a depolarized signal originating from the FRET (the specific signal which is to be measured),
- a highly polarized signal emitted by the acceptor, as a result of its direct excitation by the light beam intended to excite the donor (parasitic signal), and a highly polarized signal emitted by the donor, as a result of the excitation of the donor (parasitic signal).

The method according to the invention is therefore based on the use of this significant variation in polarization between the donor and the acceptor in order to improve the spectral selectivity of the FRET measurement. In fact, according to one of the variants of the invention, measurement of the fluorescence signal emitted is carried out either in the polarization plane parallel to that of the polarized excitation light, or in the polarization plane orthogonal to that of the polarized excitation light, according to the state of polarization of the donor molecule and that of the acceptor molecule.

The invention therefore relates to a method for detection of an energy transfer between a donor fluorescent compound and an acceptor fluorescent compound present in a measurement medium, in which the energy transfer measurement selectivity is improved by using the polarization properties of said donor and acceptor fluorescent compounds.

The energy transfer is detected by measuring the signal resulting from the florescence emitted by the acceptor fluorescent compound at a wavelength $\lambda 3$. This emission results from the energy transfer between a donor fluorescent compound, excited in the measurement medium at a wavelength $\lambda 1$ and said acceptor fluorescent compound.

By "measurement medium", is meant a solution comprising the donor and acceptor fluorescent compounds; this solution can be a biological sample, or it can contain the elements necessary for studying a biological phenomenon.

The measurement medium can also be a sample of living tissue or living cells, placed in an appropriate culture medium. In this case, the donor and acceptor fluorescent compounds are present either in the culture medium of said sample of tissue or said cells, or in the tissue itself or in the cells.

The measurement medium can finally be constituted by a living organism, an animal, in particular a mammal to which the donor and acceptor fluorescent compounds have been administered. The administration of the donor and acceptor fluorescent compounds to a living animal can be carried out topically, by simply bringing said compounds into contact with the animal; the donor and acceptor compounds can also be injected into the animal; the donor and acceptor fluorescent compounds can also be directly produced in the animal's organism by genetic engineering.

As shown in the rest of the description, the general method according to the invention makes it possible to resolve the problems linked to the use of donor and acceptor fluorescent compounds with low spectral selectivity, and in particular to limit the noise linked on the one hand to the emission of light by the donor at the emission wavelength of the acceptor, and on the other hand to the emission of light by the acceptor not involved in the energy transfer, the acceptor being in this case excited directly by the exciting light.

DETAILED DESCRIPTION OF THE INVENTION

According to a first aspect, the invention relates to a method for detecting an energy transfer between a donor fluorescent compound and an acceptor fluorescent compound present in a measurement medium, comprising the following stages:

(i) excitation of the measurement medium by a light beam polarized at the wavelength $\lambda 1$, $\lambda 1$ being the wavelength at which said donor fluorescent compound is excited, and (ii) measurement of the signal resulting from the fluorescence emitted at the wavelength $\lambda 3$ in a polarization plane different from the polarization plane of the exciting light, $\lambda 3$ being the wavelength at which the fluorescence of the acceptor fluorescent compound is emitted, said method being characterized in that moreover it comprises the following stages:

(iii) measurement of the signal resulting from the fluorescence emitted at the wavelength $\lambda 2$, $\lambda 2$ being the wavelength at which the fluorescence of the donor fluorescent compound is emitted, and (iv) correction of the signal resulting from the fluorescence emitted by the acceptor fluorescent compound at wavelength $\lambda 3$ by the signal resulting from the fluorescence emitted by the donor fluorescent compound at wavelength $\lambda 2$, in that the exciting light is polarized, and in that the signal resulting from the fluorescence emitted at the wavelength $\lambda 3$ is measured in a plane different from the polarization plane of the exciting light.

Measurement of the signal emitted at the emission wavelength of the acceptor fluorescent compound in a plane different from (i.e. not parallel to) the polarization plane of the exciting light, will make it possible to measure the signal emitted by the strongly depolarized species, and in particular the signal from the acceptor involved in the energy transfer, thus reducing the part of the measured signal not originating from the energy transfer. The plane in which the measurement is carried out is preferentially the plane orthogonal to the polarization plane of the exciting light. Measurements in other planes could also be suitable.

The correction of stage (iv) above can, for example, consist of a calculation of the ratio of the intensity of the fluorescence measured at the wavelength $\lambda 3$ to that measured at the wavelength $\lambda 2$.

In the case where a measurement of fluorescence at the emission wavelength of the donor ($\lambda 2$) is carried out, measurement of the signal resulting from the emitted fluorescence can be carried out in a parallel or different plane, preferably orthogonal to the plane of the exciting light.

In a second embodiment, the polarization properties of the donor and acceptor fluorescent compounds are used in order to improve the energy transfer measurement selectivity, in a method intended to determine the polarization variation due to the energy transfer. As in the first method described above, this method will make it possible to improve the measurement selectivity, which is thus better correlated to the energy transfer phenomenon which is to be detected.

This second embodiment comprises the following stages:

(i) excitation of the measurement medium by a light beam polarized at the wavelength $\lambda 1$, $\lambda 1$ being the wavelength at which said donor fluorescent compound is excited, (ii) measurement of the total fluorescence intensity $(It_{//})_{\lambda 2}$ emitted at the wavelength $\lambda 2$ in the plane parallel to the plane of the exciting light, $\lambda 2$ being the wavelength at which the donor fluorescent compound light is emitted, (iii) measurement of the total fluorescence intensity $(It_{\perp})_{\lambda 2}$ emitted at the wavelength $\lambda 2$ in a plane different from the polarization plane of the exciting light, (iv) measurement of the total fluorescence intensity $(It_{//})_{\lambda 3}$ emitted at the wavelength $\lambda 3$ in the plane parallel to the plane of the exciting light, $\lambda 3$ being the wavelength at which the acceptor fluorescent compound light is emitted, (v) measurement of the total fluorescence intensity $(It_{\perp})_{\lambda 3}$ emitted at the wavelength $\lambda 3$ in a plane different from the polarization plane of the exciting light, (vi) calculation of the polarization P due to the energy transfer between the donor fluorescent compound and acceptor fluorescent compound according to the following formula:

$$P = \frac{[(It_{//})_{\lambda 3} - (It_{//})_{\lambda 2} \times A)] - G[(It_{\perp})_{\lambda 3} - (It_{\perp})_{\lambda 2} \times B)]}{[(It_{//})_{\lambda 3} - (It_{//})_{\lambda 2} \times A)] + nG[(It_{\perp})_{\lambda 3} - (It_{\perp})_{\lambda 2} \times B)]}$$

in which:
  A represents the proportionality factor between the signals resulting from the fluorescence emitted at wavelengths $\lambda 2$ and $\lambda 3$ by the donor alone, in a plane parallel to the plane of the exciting light,
  B represents the proportionality factor between the signals resulting from the fluorescence emitted at wavelengths $\lambda 2$ and $\lambda 3$ by the donor alone, in a plane different from the polarization plane of the exciting light, n=1 or 2. When n=1, the term polarization measurement is used; when n=2, it is a question of anisotropy.
  G is a factor making it possible to correct the difference in sensitivity of detection in the parallel and orthogonal planes. This factor is either provided by the constructor, or can be easily determined by a person skilled in the art by measuring the polarization of substances of known polarization. In a particular implementation, G is comprised between 0.1 and 2, preferably G is comprised between 0.8 and 1.2, and in particular G=1; and (vii) comparison of the calculated value of P with that obtained in a control measurement medium in which the energy transfer does not take place, a decrease in P being indicative of an energy transfer.

According to a preferred embodiment, A and B are calculated in the following manner:

$$A = (Id_{//})_{\lambda 3} - (Id_{//})_{\lambda 2}$$

$$B = (Id_{\perp})_{\lambda 3} - (Id_{\perp})_{\lambda 2}$$

$(Id_{//})_{\lambda 3}, (Id_{//})_{\lambda 2}, (Id_{\perp})_{\lambda 3}, (Id_{\perp})_{\lambda 2}$ corresponding to the fluorescence intensities emitted at wavelengths $\lambda 2$ or $\lambda 3$, in the planes parallel to or different from the polarization plane of the exciting light, by a measurement medium containing said donor fluorescent compound but not containing the acceptor fluorescent compound.

As in the first method described, the measurements carried out in a plane different from the polarization plane of the exciting light are preferentially carried out in the plane orthogonal to the polarization plane of the exciting light. Measurements in other planes could also be suitable, from the moment when the plane chosen is not the plane parallel to the polarization plane of the exciting light.

The method according to the invention therefore makes it possible to improve the selectivity of measurement of an energy transfer phenomenon between a donor compound and an acceptor compound. This is particularly advantageous in the case where the spectral selectivity between the donor and the acceptor is not optimum, i.e. in the following cases:
  case where the emission spectra of the donor and the acceptor overlap. The methods according to the invention are particularly effective in the case where 5 nm<$\lambda 3 - \lambda 2$<100 nm, $\lambda 3 - \lambda 2$ representing the difference between the wavelengths $\lambda 3$ and $\lambda 2$.
  case where a direct parasitic excitation of the acceptor is possible at the excitation wavelength of the donor ($\lambda 1$).

The method according to the invention can be implemented with numerous donor and acceptor fluorescent compounds: these compounds can be chosen from fluorescent proteins or organic fluorophores.

The donor and the acceptor can be fluorescent proteins chosen from: GFP (Green fluorescent protein), CFP (Cyan fluorescent protein), YFP (Yellow fluorescent protein) and, generally, GFP derivatives (BFP, eGFP), as well as from the family of Reef Coral Fluorescent Proteins (RCFPs) such as DsRed HcRed.

The donor and the acceptor can also be organic fluorophores, for example: rhodamines, cyanines, squaraines, fluoresceins, bodipys, compounds of the Alexa Fluor family and their derivatives, or also the fluorescent compounds described in the Application WO2003104685.

Finally, the donor and the acceptor can be fluorescent microspheres or nano-crystals of the Quantom-dot type.

These fluorescent compounds and their use in the FRET systems between a donor and an acceptor are widely described in the literature. Moreover, a person skilled in the art is able to use the method which is the subject of the present Application with a large number of donor/acceptor pairs.

In a preferred aspect, the donor and acceptor fluorescent compounds have a high polarization, in particular greater than 50 mP, preferably greater than 100 mP. The donor and acceptor compounds the intrinsic polarization of which is less than 50 mP can be coupled or adsorbed to carrier molecules (organic molecules, proteins, peptides, antibodies, or other molecules as described hereafter), which has the effect of increasing the apparent polarization of the fluorophore and makes it possible to use it in the methods according to the invention.

In another preferred aspect, the donor and acceptor fluorescent compounds are chosen such that following excitation at the excitation wavelength of the donor $\lambda 1$, no emission from the acceptor is detected at the emission wavelength of the donor $\lambda 2$.

The method according to the invention therefore makes it possible to substantially improve the detection of energy transfer phenomena, which makes it possible in particular to study more precisely the biological interactions.

The method according to the invention can thus be used in a biological system in which the distance between the donor and acceptor fluorescent compounds varies as a function of a biochemical event taking place in the measurement medium.

In a preferred implementation, the donor and acceptor fluorescent compounds are bound to molecules chosen from the group comprising: a peptide, a protein, an antibody, an antigen, an intercellular messenger, an intracellular messenger, a hapten, a lectin, biotin, avidin, streptavidin, a toxin, a carbohydrate, an oligosaccharide, a polysaccharide, a nucleic acid. If the donor and/or acceptor fluorescent compounds are fluorescent proteins, they can be bound to other proteins in the form of fusion proteins, produced by recombinant DNA techniques well known to a person skilled in the art.

This can for example be the case if the donor and acceptor fluorescent compounds are bound directly or indirectly to a hydrolyzable substrate. If the measurement medium for example contains an enzyme capable of cleaving said substrate, the detection of the evolution of the FRET can be correlated to the enzymatic activity. It is possible to add to such a system compounds the impact of which on the enzymatic activity is to be studied, and observe the variation in the FRET, and therefore the variation in the enzymatic activity, as a function of the compounds added to the measurement medium.

By direct or indirect binding of the fluorescent compounds to the substrate, is meant a covalent bond, optionally via spacer arms, or non-covalent bonds by means of pairs of molecules capable of binding to each other. Such indirect bonds include for example the case where a fluorescent compound is bound in a covalent manner to biotin, and the substrate comprises a streptavidin group, or also the case where the fluorescent compound is bound to an antibody specific to a tag present on the substrate, such as the groups 6his, flag etc.

The method according to the invention can also be implemented in order to study the variation in a FRET in the case of an interaction between two compounds. In this case, the donor and acceptor fluorescent compounds are bound in a covalent manner to two molecules capable of recognizing each other. For example, the donor compound can be bound to an antibody or antibody fragment and the acceptor compound can be bound to the antigen recognized by this antibody. Or also, the donor and acceptor compounds are each bound to one member of a ligand-receptor pair, or to two proteins interacting with each other, or also the donor is bound to a compound regulating the activity of a protein and the acceptor compound is bound to said protein.

Finally, the method according to the invention can also be implemented in order to study the bond of two compounds X and Y to a third compound Z. This can be useful for studying complex recognition phenomena between different proteins. In this case, compound X is bound in a covalent manner to a donor fluorescent compound, compound Y is bound to an acceptor fluorescent compound, and an energy transfer takes place if X and Y are bound to the molecule Z.

In a preferred aspect, the donor and acceptor fluorescent compounds are different.

The invention finally relates to a measurement apparatus suited to the implementation of the method according to the invention.

Such an apparatus comprises the following elements:
- means of illumination of a measurement medium by a polarized exciting light, for example, lasers, flash or continuous lamps combined with a polarizer,
- means for collecting the fluorescence emitted by the measurement medium at different wavelengths and in different polarization planes, in particular parallel or non-parallel, preferentially orthogonal to that of the exciting light, the detection means being able to be photomultiplier tubes, CDD cameras or intensified cameras in front of which the appropriate polarizers are placed, and
- computer means making it possible to correct the signal measured at the emission wavelength of the acceptor fluorescent compound by that measured at the emission wavelength of the donor fluorescent compound, in particular computer programs capable of calculating the ratio of the intensity of the signal collected at the emission wavelength of the acceptor by the intensity of the signal collected at the emission wavelength of the donor.

Another apparatus making it possible to implement the method according to the invention comprises:
- means of illuminating a measurement medium by a polarized exciting light, for example, lasers, flash or continuous lamps combined with a polarizer,
- means of collecting fluorescence emitted by the measurement medium at different wavelengths and in different polarization planes, in particular parallel or non-parallel, preferentially orthogonal to that of the exciting light, the means of detection being able to be photomultiplier tubes, CDD cameras or intensified cameras in front of which the appropriate polarizers are placed, and
- computer means making it possible to calculate the polarization of the measurement medium specifically due to the energy transfer taking place in the measurement medium, according to the method described above.

These apparatuses can be for example microscopes allowing measurement of the intensity of fluorescence emitted by a sample.

The method according to the invention, its different implementations, as well as the instruments making it possible to implement this method make it possible to study in a precise manner the FRET phenomena taking place in complex measurement media and in particular biological media containing mixtures of proteins, animal or plant cells, membranes originating from animal or plant cells or artificial membranes.

The methods according to the invention basically making it possible to optimize the energy transfer (FRET) measurements, they are completely appropriate for all the techniques based on the FRET measurements.

For example, the methods according to the invention can also be implemented in order to refine the data obtained by "FLIM" (Fluorescence Lifetime Imaging Microscopy) type techniques. For this purpose, the methods according to the invention are implemented using microscopy instruments (in particular confocal microscopy systems) which make it possible both to obtain images of the cells or biological samples studied, and to measure the energy transfer phenomena.

Fluorescence lifetime imaging microscopy (FLIM) allows quantitative monitoring of the FRET with great sensitivity, via the changes induced in the lifetime of the fluorescence of the donor and/or the acceptor. More generally, it provides access to the variations in physico-chemical parameters in the immediate environment of the fluorescent probes.

The examples below illustrate the invention in a non-limitative manner.

Example 1

Determination of the Level of Polarization of Different Fluorescent Molecules

Different fluorescent molecules were used in this Experiment
- A647 (Alexa Fluor 647 from Molecular Probes).
- eGFP (Green Fluorescent Protein) protein expressed in HEK293 cells.
- V1a-YFP (Yellow Fluorescent Protein) receptor fusion protein expressed in HEK293 cells.
- CXCR4-CFP (Cyan Fluorescent Protein) receptor fusion protein expressed in HEK293 cells.
- CAM fusion protein the structure of which is as follows: CFP-peptide linker-YFP (this construction is described by Zhou et al in The Journal of Pharmacology and Experimental Therapeutics, 305:460-466, 2003 "Direct interaction between the heterotrimeric G protein subunit Gβ35 and the G protein γ subunit-like domain containing regulator of G protein signaling 11: Gain of function of cyan fluorescent protein-tagged Gγ3)." This fusion protein was also expressed in HEK 293 cells. The peptide linker can be any peptide with approximately 9 amino acids, no matter what these amino acids are.

The expression of the different fusion proteins in the HEK293 cells was realized in the following manner:

The HEK293 cells are transitorily transfected by electroporation with plasmids coding for different fusion proteins. The cells are then placed at 37° C. in a regulated medium. After 24 hours, the cells are recovered, washed in a PBS buffer, counted and fixed in a paraformaldehyde-based solution.

All the fluorescent molecules were then distributed in black Costar microplates in a volume of 100 µl in a PBS or $PO_4$ (for A647) buffer. The concentration of A647 was 10 nM. In order to measure the level of polarization of the different fluorescent proteins, 50,000 HEK293 cells containing the different molecules were distributed in the different wells of the microplate. The same quantity of control cells (containing no fluorescent protein) was distributed in "control" wells.

The level of polarization was determined using a microplate fluorescence reader, the Analyst (Molecular Devices). Depending on the fluorescent molecule to be detected, the Analyst was equipped with the following filters (all from Omega Optical):

| Molecule | Excitation | | Dichroic | Emission | |
|---|---|---|---|---|---|
| | Filter name | Wavelength | Filter name | Filter name | Wavelength |
| EGFP | XF1015 | 485 nm | 505DRLP | XF3007 | 535 nm |
| YFP (no FRET) | XF1019 | 535 nm | 570DRLP | XF3022 | 580 nm |
| A647 | XF1027 | 640 nm | 650DRLP | XF3031 | 682 nm |
| YFP (FRET) | XF1071 | 440 nm | 455DRLP | XF3079 | 535 nm |
| CFP | XF1071 | 440 nm | 455DRLP | XF3075 | 480 nm |

The successive measurement on the same well of the fluorescences emitted in the presence of polarizers inserted either between the excitation source and the sample (excitation polarizer) or between the sample and the detector (emission polarizer) will make it possible to calculate the level of polarization of the molecules. Thus two measurements of fluorescence intensity are carried out:

the so-called "parallel" fluorescence intensity ($I_{//}$) which corresponds to the fluorescence intensity measured with the emission polarizer situated in the same plane as the excitation polarizer, and the so-called "orthogonal" fluorescence intensity ($I_\perp$) which corresponds to the fluorescence intensity measured with the emission polarizer situated in a plane perpendicular to the excitation polarizer.

For each fluorescent molecule, the level of polarization (P) is then obtained by means of the following formula:

$$P=[(I_{//}-I_\perp)/(I_{//}+I_\perp)]\times 1000$$

P is expressed in mP units.

Table 1 below shows the levels of polarization obtained for the different molecules observed.

TABLE 1

| Molecule | Level of polarization |
|---|---|
| A647 | −17 mP |
| EGFP | 395 mP |
| YFP (no FRET) | 222 mP |
| YFP (FRET) | 86 mP |
| CFP | 352 mP |

The values obtained show that the polarization of the different fluorescent proteins used in the experiment is very high (>200 mP) compared with that of a small organic molecule such as Alexa Fluor 647 (−17 mP).

Example 2

Determination of the Signal/Noise (S/N) Ratio of an Intracellular FRET Experiment The following fusion proteins were used in this experiment:

V1a-YFP fusion protein receptor (YFP=Yellow Fluorescent Protein) expressed in HEK293 cells.

CXCR4-CFP fusion receptor protein (CFP=Cyan Fluorescent Protein) expressed in HEK293 cells.

CAM fusion protein the structure of which is as follows: CFP-peptide linker-YFP. This fusion protein was also expressed in HEK 293 cells.

The expression of these different proteins was carried out as described in Example 1.

The cells containing CAM are those which allow the measurement of a FRET between the CFP (donor molecule) and the YFP (acceptor molecule). In the different so-called "positive" wells of a microplate, 25,000 cells containing CAM, previously diluted in a PBS buffer, were distributed in a volume of 100 μl.

In the different so-called "negative" wells of a microplate, 50,000 cells containing V1a-YFP and 50,000 cells containing CXCR4-CFP were distributed in a PBS buffer in a total volume of 100 μl. In this case, the absence of proximity between CFP and YFP prevents any FRET between these two molecules and only the fluorescence noise is measured.

Two successive fluorescence measurements are carried out on the Analyst using the following filters:

| | Excitation | | Dichroic | Emission | |
|---|---|---|---|---|---|
| | Filter name | Wavelength | Filter name | Filter name | Wavelength |
| Measurement 1 | XF1071 | 440 nm | 455DRLP | XF3075 | 480 nm |
| Measurement 2 | XF1071 | 440 nm | 455DRLP | XF3079 | 535 nm |

These two fluorescence measurements at 480 nm ($I_{480\,nm}$) or 535 nm ($I_{535\,nm}$) will be carried out in the presence or in the absence of polarizers. In the presence of polarizers, only the so-called "orthogonal" fluorescence intensity ($I_\perp$) as defined in Example 1 is measured.

Then the ratios $R=(I_{535\,nm}/I_{480\,nm})$ are calculated for the positive or negative wells and that for the total fluorescence measurements (without polarizers) or for the orthogonal fluorescence measurement (with polarizers).

The signal/noise (S/N) of the experiment is then calculated as follows for the measurements carried out with or without the polarizers.

$$(S/B)=(R_{535/480\,positive}/R_{535/480\,negative})$$

The graph represented in FIG. 1 gives the signal/noise values obtained in the absence or in the presence of polarizers.

This shows that the use of polarizers in the detection system makes it possible to significantly increase the signal/noise ratio of the experiment (+48%).

In fact, the so-called "orthogonal" fluorescence measurement encourages the detection of the signal emitted by the acceptor after energy transfer (depolarized fluorescence) compared to the fluorescence signals emitted by fluorescence donors or acceptors not involved in a FRET phenomenon (highly polarized fluorescence).

Example 3

Measurement of the Degree of Polarization of the Acceptor for the Detection of a FRET. Correction of the Contamination of the Donor in the Measured Fluorescence Signals and Quantification of the FRET The fusion proteins used in this example are identical to those described in Example 2. Their expression was carried out as described in Example 1.

50,000 cells containing CXCR4-CFP were distributed in a PBS buffer in a total volume of 100 μl. These so-called "control" wells allow determination of the factors A and B which will be used in order to correct the fluorescence signal at 535 nm of the fluorescence signal emitted by CFP at this wavelength.

In the different so-called "negative" wells of a microplate, 50,000 cells containing V1a-YFP and 50000 cells containing CXCR4-CFP were distributed in a PBS buffer in a total volume of 100 µl. The absence of proximity between CFP and YFP prevents any FRET between these two molecules.

25,000 cells containing CAM allowing the measurement of a FRET between CFP (the donor) and YFP (the acceptor), previously diluted in a PBS buffer, were distributed in a volume of 100 µl in the different so-called "positive" wells of a microplate.

Variable quantities of cells containing CAM and cells containing CXCR4-CFP, previously diluted in a PBS buffer, were distributed in a volume of 100 µl in the different so-called "contaminated" wells of a microplate. The mixtures were produced in the following proportions:

|  | Number of CAM cells/well | Number of CXCR4-CFP cells/well |
| --- | --- | --- |
| Contaminated 1 | 25,000 | 50,000 |
| Contaminated 2 | 12,500 | 50,000 |
| Contaminated 3 | 6,250 | 50,000 |

Each series of so-called "contaminated" wells contains a variable proportion of molecules involved in a FRET (CAM) and of free donors (CFP).

In order to determine the degree of polarization of the acceptor, four successive fluorescence measurements are carried out on the Analyst using the filters and polarizers described in the table below.

|  | Excitation | | | Emission | | |
| --- | --- | --- | --- | --- | --- | --- |
|  | Filter name | Wavelength | Dichroic Filter name | Filter name | Wavelength | Polarizer |
| Measurement 1 | XF1071 | 440 nm | 455DRLP | XF3075 | 480 nm | Parallel |
| Measurement 2 | XF1071 | 440 nm | 455DRLP | XF3075 | 480 nm | Orthogonal |
| Measurement 3 | XF1071 | 440 nm | 455DRLP | XF3079 | 535 nm | Parallel |
| Measurement 4 | XF1071 | 440 nm | 455DRLP | XF3079 | 535 nm | Orthogonal |

For the different samples, the level of overall polarization at 535 nm ($P_{overall}$) is then obtained by means of the following formula:

$$P_{overall} = [(I_{535\,nm//} - I_{535\,nm\perp})/(I_{535\,nm//} + I_{535\,nm\perp})] \times 1000$$

P is expressed in mP.

$I_{535\,nm//}$ is the fluorescence intensity obtained during measurement 3 either on the positive wells or on the negative wells or on the contaminated wells.

$I_{535\,nm\perp}$ is the fluorescence intensity obtained during measurement 4 either on the positive wells or on the negative wells or on the contaminated wells.

The degree of overall polarization measured at 535 nm represents the sum of the degree of polarization of the YFP acceptor involved in the FRET and the degree of polarization of the CFP donor measured at 535 nm due to the strong CFP signal contamination at this wavelength.

The determination of the degree of polarization of the YFP acceptor involved in the FRET can be obtained by subtracting from the signals obtained in the fluorescence measurements at 535 nm (measurements 3 and 4) the part of the signal originating from the CFP donor.

This can be carried out by establishing a proportionality between the signal emitted by CFP at 480 nm with the different polarizers (measurements 1 and 2) and the signal that it emits at 535 nm on the control wells described above. For this purpose the following formulae are used:

$$A = (It_{535\,nm//}/It_{480\,nm//})$$

$$B = (It_{535\,nm\perp}/It_{480\,nm\perp})$$

$It_{480\,nm//}$ is the mean of the fluorescence intensities obtained during measurement 1 on the control wells.

$It_{480\,nm\perp}$ is the mean of the fluorescence intensities obtained during measurement 2 on the control wells.

$It_{535\,nm//}$ is the mean of the fluorescence intensities obtained during measurement 3 on the control wells.

$It_{535\,nm\perp}$ is the mean of the fluorescence intensities obtained during the measurement 4 on the control wells.

The fluorescence signals of the YFP acceptor involved in the FRET obtained at 535 nm with the different configurations of polarizers ($If_{535\,nm//}$ and $If_{535\,nm\perp}$) are then calculated using the following formulae for the different samples tested:

$$If_{535\,nm//} = I_{535\,nm//} - (I_{480\,nm//} \times A)$$

$$If_{535\,nm\perp} = I_{535\,nm\perp} - (I_{480\,nm\perp} \times B)$$

$I_{480\,nm//}$ is the fluorescence intensity obtained during measurement 1 either on the positive wells or on the negative wells or on the contaminated wells.

$I_{480\,nm\perp}$ is the fluorescence intensity obtained during measurement 2 either on the positive wells or on the negative wells or on the contaminated wells.

$I_{535\,nm//}$ is the fluorescence intensity obtained during measurement 3 either on the positive wells or on the negative wells or on the contaminated wells.

$I_{535\,nm\perp}$ is the fluorescence intensity obtained during measurement 4 either on the positive wells or on the negative wells or on the contaminated wells.

The degree of polarization of the YFP acceptor involved in the FRET (Pf) is then calculated for the positive, negative or contaminated wells using the following formula:

$$Pf = [(If_{535\,nm//} - If_{535\,nm\perp})/(If_{535\,nm//} - If_{535\,nm\perp})] \times 1000$$

Pf is expressed in mP.

Table 2 below gives the degree of overall polarization ($P_{overall}$) and the degree of polarization of the YFP acceptor involved in the FRET (Pf) for the different samples:

TABLE 2

|  | $P_{overall}$ | Pf |
| --- | --- | --- |
| Negative | 289 mP | 322 mP |
| Positive | 84 mP | −42 mP |

TABLE 2-continued

|  | $P_{overall}$ | Pf |
| --- | --- | --- |
| Contaminated 1 | 129 mP | −45 mP |
| Contaminated 2 | 154 mP | −51 mP |
| Contaminated 3 | 182 mP | −54 mP |

The values shown in Table 2 above show that the formulae described previously make it possible to recalculate from different polarized fluorescence measurements the degree of polarization of the acceptor involved in the FRET even if the sample contains a large quantity of CFP donor not involved in an energy transfer.

The degree of polarization of YFP in the FRET, situated around −50 mP in our experiment, also confirms that the YFP acceptor is strongly depolarized when it is involved in a FRET (initial polarization value 222 mP found in Example 1).

CITED BIBLIOGRAPHY

1. Sato et al. (2002) Nature Biotechnology, 20, 287-294.
2. Giulano et al. (1998) Tibtech, 16, 135-140.
3. Miyawaki (2003) Developmental Cell, 4, 295-305.
4. Sokol et al. (1998) PNAS, 95, 11538-11543.
5. Chan et al. (1979) J Histochem Cytochem, 27-1, 56-64.
6. Miyawaki et al. (1997) Nature, 388, 882-887.
7. Bastiaens (2000) Patent WO 00/43780.
8. He et al (2003) Cytometry part A, 53A, 39-54.
9. Gaits et al. (2003) Science's STKE, www.stke.org/cgi/content/full/sigtrans; 2003/165/pe3.
10. Yishai et al. (2003) Phys. Med. Biol, 48, 2255-2268.
11. Clayton et al. (2002) Biophysical Journal, 83, 1631-1649.
12. Ventre et al. (2003) Molecular Microbiology, 48(1), 187-198.
13. Knight et al. (2002) J. Biochem. Biophys. Methods, 51, 165-177.

The invention claimed is:

1. Method for detecting an energy transfer between a donor fluorescent compound and an acceptor fluorescent compound present in a measurement medium, comprising the following steps:
   (i) exciting the measurement medium by a light beam at a wavelength $\lambda 1$, wherein $\lambda 1$ is the wavelength at which said donor fluorescent compound is excited,
   (ii) measuring the signal resulting from the fluorescence emitted at a wavelength $\lambda 3$, wherein $\lambda 3$ is the wavelength at which the fluorescence of the acceptor fluorescent compound is emitted,
   (iii) measuring the signal resulting from the fluorescence emitted at a wavelength $\lambda 2$, wherein $\lambda 2$ is the wavelength at which the fluorescence of the donor fluorescent compound is emitted, and
   (iv) correcting the signal resulting from the fluorescence emitted by the acceptor fluorescent compound at the wavelength $\lambda 3$ by the signal resulting from the fluorescence emitted by the donor fluorescent compound at the wavelength $\lambda 2$,
   wherein the donor fluorescent compound and the acceptor fluorescent compound are different,
   the exciting light beam is polarized, and
   the signal resulting from the fluorescence emitted at the wavelength $\lambda 3$ is measured in a plane different from the polarization plane of the exciting light.

2. Method according to claim 1, wherein the signal resulting from the fluorescence emitted at the wavelength $\lambda 2$ is measured in a plane different from the polarization plane of the exciting light.

3. Method according to claim 1 or 2, wherein the correction of the signal resulting from the fluorescence emitted by the acceptor fluorescent compound at the wavelength $\lambda 3$ by the signal resulting from the fluorescence emitted by the donor fluorescent compound at the wavelength $\lambda 2$ comprises the determination of the ratio of the signals measured at the wavelengths $\lambda 3$ and $\lambda 2$.

4. Apparatus for measuring the fluorescence resulting from an energy transfer between a donor fluorescent compound and an acceptor fluorescent compound present in a measurement medium, comprising:
   means for illuminating said medium by a polarized exciting light,
   means for collecting the fluorescence emitted by the medium at different wavelengths and in different polarization planes that are parallel or non-parallel, to the plane of the exciting light and
   computer means for calculating the polarization of the measurement medium specifically due to the energy transfer taking place in the measurement medium, according to the method described in claim 3.

5. Apparatus according to claim 4, wherein said apparatus is a microscope.

6. The apparatus according to claim 4, wherein the different polarization planes are orthogonal to that of the exciting light.

7. Method according to claim 1, wherein the signals resulting from the fluorescence emitted at the wavelengths $\lambda 2$ and/or $\lambda 3$ are measured in a plane orthogonal to the polarization plane of the exciting light.

8. Method according to claim 1, further comprising the following steps:
   (i) exciting the measurement medium by a light beam polarized at the wavelength $\lambda 1$, wherein $\lambda 1$ is the wavelength at which said donor fluorescent compound is excited,
   (ii) measuring the total fluorescence intensity $(It_{//})_{\lambda 2}$ emitted at the wavelength $\lambda 2$ in a plane parallel to the plane of the exciting light, wherein $\lambda 2$ is the wavelength at which the donor fluorescent compound light is emitted,
   (iii) measuring the total fluorescence intensity $(It_{\perp})_{\lambda 2}$ emitted at the wavelength $\lambda 2$ in a plane different from the polarization plane of the exciting light,
   (iv) measuring the total fluorescence intensity $(It_{//})_{\lambda 3}$ emitted at the wavelength $\lambda 3$ in a plane parallel to the plane of the exciting light, wherein $\lambda 3$ is the wavelength at which the acceptor fluorescent compound light is emitted,
   (v) measuring the total fluorescence intensity $(It_{\perp})_{\lambda 3}$ emitted at the wavelength $\lambda 3$ in a plane different from the polarization plane of the exciting light,
   (vi) calculating the polarization P due to the energy transfer between the donor fluorescent compound and acceptor fluorescent compound according to the following formula:

$$P = \frac{[(It_{//})_{\lambda 3} - (It_{//})_{\lambda 2} \times A)] - G[(It_{\perp})_{\lambda 3} - (It_{\perp})_{\lambda 2} \times B)]}{[(It_{//})_{\lambda 3} - (It_{//})_{\lambda 2} \times A)] + nG[(It_{\perp})_{\lambda 3} - (It_{\perp})_{\lambda 2} \times B)]}$$

wherein:
   A is the proportionality factor between the signals resulting from the fluorescence emitted at the wavelengths $\lambda 2$ and $\lambda 3$ by the donor alone, in a plane parallel to the plane of the exciting light, B is the proportionality factor between the signals resulting from the fluorescence emitted at the wavelengths $\lambda 2$ and $\lambda 3$ by the donor alone, in a plane different from the polarization plane of the exciting light, n=1 or 2, G is a sensitivity correction factor specific to the measurement apparatus used, and has a value between 0.1 and 2, and (vii) comparing the calculated value of P with that obtained in a control measurement medium in which the energy transfer does not take place.

9. Method according to claim 8, wherein, in step (vi), the polarization P is calculated according to the formula:

$$P = \frac{[(It_{//})_{\lambda 3} - (It_{//})_{\lambda 2} \times A)] - G[(It_{\perp})_{\lambda 3} - (It_{\perp})_{\lambda 2} \times B)]}{[(It_{//})_{\lambda 3} - (It_{//})_{\lambda 2} \times A)] + nG[(It_{\perp})_{\lambda 3} - (It_{\perp})_{\lambda 2} \times B)]}$$

wherein:

n=1 or 2

G is a sensitivity correction factor specific to the measurement apparatus used, and has a value between 0.1 and 2, and $A = (Id_{//})_{\lambda 3} - (Id_{//})_{\lambda 2}$ $B = (Id_{\perp})_{\lambda 3} - (Id_{\perp})_{\lambda 2}$ $(Id_{//})_{\lambda 3}$, $(Id_{//})_{\lambda 2}$, $(Id_{\perp})_{\lambda 3}$, $(Id_{\perp})_{\lambda 2}$ correspond to the fluorescence intensities emitted at the wavelengths $\lambda 2$ or $\lambda 3$, in the planes parallel to (//) or different from ($\perp$) the plane of the exciting light, by a measurement medium containing said donor fluorescent compound but not the acceptor fluorescent compound.

10. Method according to claim 8 or 9, wherein said plane different from the polarization plane of the exciting light is a plane orthogonal to said polarization plane of the exciting light.

11. Method according to claim 1, wherein 5 nm<$\lambda 3-\lambda 2$<100 nm.

12. Method according to claim 1, wherein the donor and acceptor fluorescent compounds are fluorescent proteins or organic fluorophores.

13. Method according to claim 1, wherein the donor and acceptor fluorescent compounds are rhodamines, cyanines, squaraines, bodipys, fluoresceins, GFP, CFP, YFP, BFP, eGFP, RCFPs, DsRed, HcRed, Alexa fluors or their derivatives.

14. Method according to claim 1, wherein the donor and acceptor fluorescent compounds have a polarization greater than 50 mP.

15. Method according to claim 14, wherein the donor and acceptor fluorescent compounds have a polarization greater than 100 mP.

16. Method according to claim 1, wherein the donor and acceptor fluorescent compounds are selected such that following excitation at the excitation wavelength of the donor $\lambda 1$, no emission of the acceptor is detected at the emission wavelength of the donor $\lambda 2$.

17. Method according to claim 1, wherein the distance between the donor and acceptor compounds varies as a function of biochemical events taking place in the measurement medium.

18. Method according to claim 1, wherein the donor and acceptor fluorescent compounds are bound to molecules including peptides, proteins, antibodies, antigens, intercellular messengers, intracellular messengers, hapten, lectin, biotin, avidin, streptavidin, toxin, carbohydrate, oligosaccharide, polysaccharide, or a nucleic acid.

19. Method according to claim 1, wherein the donor and acceptor compounds are bound directly or indirectly to a hydrolyzable substrate.

20. Method according to claim 1 wherein the donor and acceptor compounds are each bound in a covalent manner to a pair of molecules capable of recognizing each other.

21. Method according to claim 1, wherein the donor and acceptor compounds are each bound to two molecules capable of recognizing a third molecule present in the measurement medium.

22. Apparatus for measuring the fluorescence resulting from an energy transfer between a donor fluorescent compound and an acceptor fluorescent compound present in a measurement medium comprising:

means for illuminating said medium by a polarized exciting light, means for collecting the fluorescence emitted by the medium at different wavelengths and in different polarization planes, that are parallel or non-parallel, to the plane of the exciting light and computer means for correcting the signal measured at the emission wavelength of the acceptor fluorescent compound by the signal measured at the emission wavelength of the donor fluorescent compound.

23. Apparatus according to claim 22, wherein said apparatus is a microscope.

24. The apparatus according to claim 22, wherein the different polarization planes are orthogonal to that of the exciting light.

* * * * *